(12) United States Patent
Sviripa et al.

(10) Patent No.: US 9,895,324 B2
(45) Date of Patent: Feb. 20, 2018

(54) HALOGENATED DIARYLACETYLENES AND METHODS OF TREATING CANCER

(71) Applicant: UNIVERSITY OF KENTUCKY RESEARCH FOUNDATION, Lexington, KY (US)

(72) Inventors: Vitaliy M. Sviripa, Lexington, KY (US); Wen Zhang, Lexington, KY (US); Chunming Liu, Lexington, KY (US); David Watt, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/668,865

(22) Filed: Mar. 25, 2015

(65) Prior Publication Data

US 2015/0272908 A1 Oct. 1, 2015

Related U.S. Application Data

(60) Provisional application No. 61/970,657, filed on Mar. 26, 2014.

(51) Int. Cl.
*A61K 31/136* (2006.01)

(52) U.S. Cl.
CPC .................................. *A61K 31/136* (2013.01)

(58) Field of Classification Search
CPC .................................................. A61K 31/136
See application file for complete search history.

(56) References Cited

U.S. PATENT DOCUMENTS 6,951,889 B2 * 10/2005 Hansen et al. ................. 514/564
8,664,276 B2 3/2014 Watt et al.
8,716,355 B2 5/2014 Tsai

FOREIGN PATENT DOCUMENTS

| JP | 08-184867 | * | 7/1996 | .............. C09K 9/02 |
|---|---|---|---|---|
| WO | 2001029011 | A2 | 4/2001 | |
| WO | 2008073350 | A2 | 6/2008 | |
| WO | 2009038759 | A2 | 3/2009 | |
| WO | 2010092043 | A1 | 8/2010 | |
| WO | 2012149048 | A1 | 11/2012 | |
| WO | 2012149049 | A1 | 11/2012 | |

OTHER PUBLICATIONS

Yu et al 'Synthesis or 2-arylindole derivatives and evaluation as nitric oxide syntase and NFKB inhibitors' Organic and Biomolecular Chemistry, vol. 10, p. 8835-8847, 2012.*
English machine translation of JP 08-184867.*
Peckham et al 'Oxford Textbook of Oncology' Oxford University Press, vol. 1, p. 451, 1995.*
Hadfield, J.A. et al., "Preparation and Evaluation of Diarylalkynes as Antitumour Agents", Synthetic Communications: An International Journal for Rapid Communication of Synthetic Organic Chemistry. vol. 28:8. pp. 1421-1431. 1998.
Oldham, J.W. et al., "Genetic Toxicity of a Pharmacologically Active Group of ortho-(Arylalkynyl) phenoxypropanolamines." Fundamental and Applied Toxicology. vol. 14. pp. 376-385. 1990.
Sviripa, V.M. et al., "Halogenated Diarylacetylenes Repress c-myc Expression in Cancer Cells." Bioorganic Medicinal Chemistry Letters. vol. 24. pp. 3638-3640. 2014.
Zhang, W. et al. "Fluorinated N,N-Dialkylaminostilbenes for Wnt Pathway Inhibition and Colon Cancer Repression." Journal of Medicinal Chemistry. vol. 54. pp. 1288-1297. 2011.
Zhang, W. et al., "Fluorinated N,N-Dialkylaminostilbenes Repress Colon Cancer by Targeting Methionine S-Adenosyltransferase 2A." ACS Chemical Biology. vol. 8. pp. 796-803. 2013.

* cited by examiner

*Primary Examiner* — Craig D Ricci
*Assistant Examiner* — Christopher R Stone
(74) *Attorney, Agent, or Firm* — McDermott Will & Emery LLP

(57) ABSTRACT

Halogenated diarylacetylenes, e.g., diarylacetylenes having at least one halo substituent in one aryl ring and an amine in the opposing aryl ring, can inhibit the proliferation of LS174T colon cancer cells through the inhibition of c-myc and induction of the cyclin-dependent kinase inhibitor-1 (i.e., p21(Wif1/Cip1)). Such compounds are useful as antineoplastic agents.

12 Claims, 2 Drawing Sheets

HALOGENATED DIARYLACETYLENES AND METHODS OF TREATING CANCER

CROSS-REFERENCE TO RELATED APPLICATION

This application claims the benefit of U.S. Provisional Application No. 61/970,657 filed Mar. 26, 2014 the entire disclosure of which is hereby incorporated by reference herein.

STATEMENT REGARDING FEDERALLY SPONSORED RESEARCH

This invention was made with government support under R21 CA139359 and R01 CA172379. The Government has certain rights in the invention.

TECHNICAL FIELD

The present disclosure relates to halogenated diarylacetylenes for use as antineoplastic agents.

BACKGROUND

A family of fluorinated N,N-dialkylaminostilbene analogs (FIDAS agents) that inhibit the expression of Wnt target genes, such as c-myc, and repress colon cancer cell growth in vitro and in vivo was recently described. See, e.g., *J Med Chem* 2011: 54:1288-1297; *ACS Chem Biol* 2013: 8(4):796-803; U.S. Pat. No. 8,664,276.

In addition, certain diarylacetylenes are known for certain medicinal uses. See, e.g., WO2012149049; WO2012149048; WO2010092043; WO2009038759; WO2008073350; and WO2001029011. Further, U.S. Pat. No. 8,716,355 to Tsai discloses hydroxylated tolans and related compounds in the treatment of cancer and Hadfield et al disclose preparation and evaluation of diarylalkynes as antitumor agents. Hadfield et al, *Synthetic Communications* 1998: 28(8):1421-1431. However, there is an ongoing need for additional compounds that can be used to treat cancer and other ailments.

SUMMARY OF THE DISCLOSURE

Advantages of the present disclosure include halogenated diarylacetylenes and compositions having antineoplastic activity and methods of inhibiting cancer cell growth and/or treating cancer in a patient by administering one or more of the halogenated diarylacetylenes or pharmaceutical compositions thereof.

One aspect of the present disclosure is directed to halogenated diarylacetylenes that are useful for killing hyperproliferating cells such as cancer cells for the treatment of human malignant and benign cancers, including without limitation, colorectal cancer (CRC), breast cancer, lung cancer, prostate cancer and liver cancer. In this aspect of the disclosure, there are provided certain halogenated diarylacetylenes having anti-neoplastic activity against cancerous cells. The halogenated diarylacetylenes of the present disclosure include compounds according to formula (I):

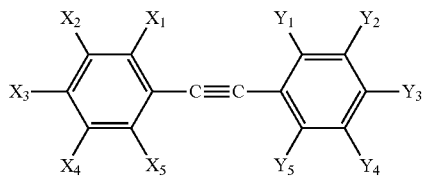

or a pharmaceutically acceptable salt thereof, wherein each of $X_1$ through $X_5$ independently represents H, a lower alkyl, or halo, provided that at least one of $X_1$ through $X_5$ is a halo; and each of $Y_1$ through $Y_5$ independently represents H, a lower alkyl, or $NR_1R_2$, provided that at least one of $Y_1$ through $Y_5$ is $NR_1R_2$, wherein each of $R_1$ and $R_2$ independently represents H, or a lower alkyl. In one aspect, of the present disclosure the compound of formula (I) does not include groups such as ester, hydroxyl, sulfonamide, amide, urethane, and carboxyl groups.

The halogenated diarylacetylenes of formula (I) or pharmaceutically acceptable salts thereof can be included in a pharmaceutical composition with a pharmaceutically acceptable carrier.

Another aspect of the present disclosure is directed to methods of treating cancer, e.g., inhibiting cancer cell growth and/or inhibiting tumor growth in a mammal, such as a human, or treating diseases associated with hyperproliferating cells. In one embodiment of this aspect of the disclosure, an effective amount of one or more halogenated diarylacetylenes, pharmaceutical salts and/or pharmaceutical compositions thereof is administered to a patient in need of treatment of cancer sufficient to treat/inhibit cancer cell growth in the patient.

In an embodiment of this aspect of the disclosure, a therapeutically effective amount of one or more halogenated diarylacetylenes, pharmaceutical salts and/or pharmaceutical compositions thereof is administered to a patient suffering from colorectal cancer. In another embodiment, a therapeutically effective amount of one or more halogenated diarylacetylenes, pharmaceutical salts and/or pharmaceutical compositions thereof is administered to a patient suffering from liver cancer or prostate cancer.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein.

DETAILED DESCRIPTION OF THE DISCLOSURE

Figure 1:
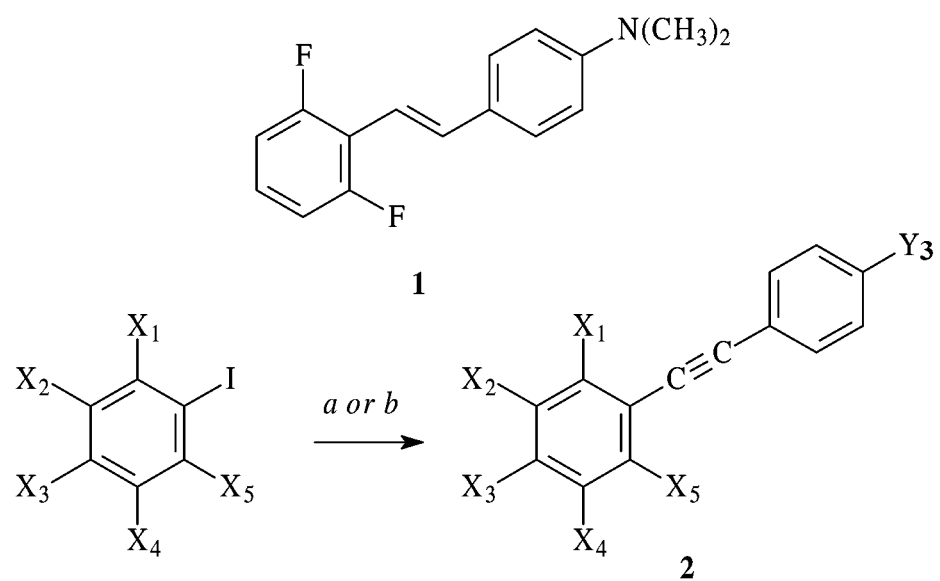
FIG. 1 is a schematic illustration of the synthesis of halogenated diarylacetylenes 2. Reagents: a, HC≡CHC$_6$H$_4$Y; 0.5% Pd(PPh$_3$)$_4$, 1% CuI, H$_2$O, 75° C., 1-2 h; b, a, HC≡CHC$_6$H$_4$NH$_2$; 0.5% Pd(PPh$_3$)$_4$, 1% CuI, H$_2$O, 75° C., 1-2 h followed by CH$_3$I, K$_2$CO$_3$, acetone, 5 h, 56° C.

The present disclosure relates to halogenated diarylacetylenes, their salts and their pharmaceutical compositions and methods of inhibiting cancer cell growth and/or treating cancer in a patient by administering one or more of the halogenated diarylacetylenes, a pharmaceutical salt thereof, or a pharmaceutical composition thereof. It was found that halogenated diarylacetylenes having at least one, preferably two, halo substituents in one aryl ring and an amine in the opposing aryl ring, e.g., N-methylamino or N,N-dimethylamino, inhibit the proliferation of LS174T colon cancer cells through the inhibition of c-myc and induction of the cyclin-dependent kinase inhibitor-1 (i.e., p21(Wif1/Cip1)). Such compounds and compositions are useful as antineoplastic agents.

The halogenated diarylacetylenes of the present disclosure include at least one amine group, e.g., a primary, secondary or tertiary amine, on the aryl ring. Such compounds are useful as antineoplastic agents and can be represented by the following formula:

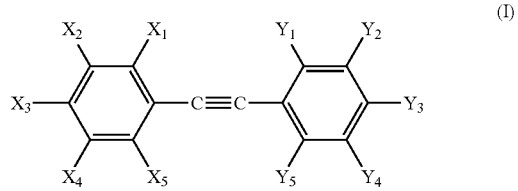

(I)

or a pharmaceutically acceptable salt thereof. The substituents of $X_1$ through $X_5$ each independently represent H, a lower alkyl, or halo, provided that at least one of $X_1$ through $X_5$ is a halo. A halo group means an F, Cl, Br, I, or At group. Preferably substituents $X_1$ through $X_5$ include at least two halo groups, e.g., an F and/or Cl. Each of $Y_1$ through $Y_5$ independently represents H, a lower alkyl, or $NR_1R_2$, provided that at least one of $Y_1$ through $Y_5$ is $NR_1R_2$, wherein each of $R_1$ and $R_2$ independently represents H, or a lower alkyl. In one aspect, of the present disclosure the compound of formula (I) does not include groups such as ester, hydroxyl, sulfonamide, amide, urethane, and carboxyl groups.

The term "lower alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups having from one to about ten carbons ($C_1$-$C_{10}$), e.g., from one to about six carbon atoms ($C_1$-$C_6$) in its backbone structure. In one aspect of the present disclosure, the lower alkyl groups specifically include methyl, ethyl, propyl, isopropyl, n-butyl, etc.

Embodiments of the halogenated diarylacetylenes of the present disclosure include wherein at least two of $X_1$ through $X_5$ is are halo groups, e.g., wherein $X_1$ through $X_5$ is either (i) a fluoro and chloro, (ii) both fluoro, (iii) both chloro groups, and wherein both $R_1$ and $R_2$ are lower alkyl groups, e.g., methyl, ethyl, or butyl groups. Preferably $X_1$ and/or $X_5$ are halo groups, e.g., the diarylacetylenes have one or two halogen substituents at ortho-positions relative to the acetylenic linkage, and $X_2$ through $X_4$ are H or a lower alkyl. In some embodiments, the halogenated diarylacetylenes include compounds, or a pharmaceutically acceptable salt thereof, where $Y_3$ is $NR_1R_2$, and $Y_1$, $Y_2$, $Y_4$, and $Y_5$ independently represent H, a lower alkyl, or $NR_1R_2$. In other embodiments, $Y_3$ is $NR_1R_2$, and $Y_1$, $Y_2$, $Y_4$, and $Y_5$ independently represent H or a lower alkyl, e.g. $Y_1$, $Y_2$, $Y_4$, and $Y_5$ represent H. In still further embodiments, at least one of $R_1$, or $R_2$, is a lower alkyl.

In another embodiment of the present disclosure, the halogenated diarylacetylenes include compounds according to formula (II):

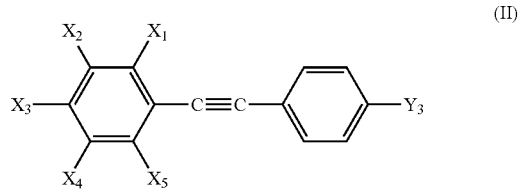

(II)

or a pharmaceutically acceptable salt thereof, wherein $Y_3$ is $NR_1R_2$, and $R_1$, $R_2$, $X_1$ through $X_5$ and are as defined for the compounds of formula (I) including the various embodiments for formula (I). Preferably, at least one of $R_1$, or $R_2$, is a lower alkyl and at least two of $X_1$ through $X_5$ are either (i) a fluoro and chloro, (ii) both fluoro, (iii) both chloro groups. In another embodiment, both $R_1$, and $R_2$, are lower alkyl, e.g., methyl, and at least two of $X_1$ through $X_5$ are either: (i) a fluoro and chloro, (ii) both fluoro, (iii) both chloro groups. In some embodiments, $X_1$ and/or $X_5$ are halo groups, e.g., either a fluoro or chloro group.

Pharmaceutical compositions of the present disclosure include one or more of compounds according to formula (I) or a pharmaceutically acceptable salt thereof and a pharmaceutically acceptable carrier. Preferable, pharmaceutical compositions of the present disclosure include one or more of compounds according to formula (II) and a pharmaceutically acceptable carrier.

In one aspect of the present disclosure, the compounds of formula (I) or (II), a pharmaceutically acceptable salt thereof, or a pharmaceutically acceptable composition thereof is used in the treatment of cancer. The method comprises administering to a patient in need of such treatment an effective amount of one or more of the halogenated diarylacetylenes, a pharmaceutical salt thereof, or a pharmaceutical composition thereof. Embodiments of the method include wherein the cancer treated is selected from the group consisting of colorectal cancer, breast cancer, lung cancer, prostate cancer and liver cancer.

In the course of developing new agents for the treatment of cancers, we identified a family of fluorinated N,N-dialkylaminostilbene analogs (FIDAS agents) that inhibit the expression of Wnt target genes, such as c-myc, and repress colon cancer cell growth in vitro and in vivo. Recently, we found that (E)-4-(2',6'-difluorostyryl)-N,N-dimethylaniline (1) (FIG. 1) targeted exclusively the catalytic subunit of methionine S-adenosyltransferase-2 (MAT-2). See Zhang et al. *ACS Chem Biol* 2013: 8(4):796-803. MAT-2 serves as a source of S-adenosylmethionine (SAM) in colorectal and liver cancers where MAT-2 is upregulated. See Cai et al. *Hepatology* 1996: 24:1090-1097; Chen et al. *Gastroenterology* 2007: 133:207-218; Ito et al. *Surg Today* 2000: 30:706-710; and Liu et al. *J Biol Chem* 2011: 286: 17168-17180.

It is believed that neoplastic tissues make effective use of SAM from this isoform of MAT to manage crucial epigenetic modifications of histone proteins and thereby regulate gene expression. Interference with this process would represent a new approach for developing potential antineoplastic agents. It is believed that the compounds of the present disclosure inhibit c-myc. In addition, the present compounds would avoid the facile E/Z-isomerizations that afflict the stilbenes and complicate pharmacodynamic and pharmacokinetic studies.

The diarylacetylenes 2 (FIG. 1), e.g., compounds of formula (II), are a preferred group of halogenated diarylacetylenes. Prior reports of acetylenic compounds as antineoplastic agents include monoalkylacetylenes from aquatic organisms and diarylacetylenic analogs of combrestatin. See Dembitsky et al. *Nat. Prod. Commun.* 2006: 1:773-812 and Hadfield et al. *Synth. Commun.* 1998: 28:1421-1431. The latter compounds showed cytotoxic activity against a murine leukemia cell line and one showed activity as an inhibitor of tubulin polymerization. The Sonogashira coupling of 4-(N,N-dimethylamino)phenylacetylene with various aryl iodides provided access to the desired diarylacetylenes 2 (Table 1). (Additional information about Sonogashira coupling can be found in Bhattacharya et al. Sengupta, S. *Tetrahedron Lett.* 2004: 47:8733-8736 and Okuro et al. *J. Org. Chem.* 1993: 58:4716-4721). Prior work from our laboratories established that stilbenes with N-methylamino and N,N-dimethylamino groups in a para-orientation relative to the central double bond as well as 2,6-difluoro, 2-chloro-6-fluoro or 2,6-dichloro halogenation patterns in the other aromatic ring were the most potent analogs in the inhibition of LS174T cell proliferation. See Zhang et al. *J Med Chem* 2011: 54:1288-1297.

Table 1 below provides $IC_{50}$ values for the inhibition of LS174T cell proliferation for certain halogenated diarylacetylenes of the present disclosure and stilbene compound 1 as shown in FIG. 1.

TABLE 1

| Compound | $X_1$ | $X_2$ | $X_3$ | $X_4$ | $X_5$ | $Y_3$ | Inhibition of LS174T Cell Proliferation $IC_{50}$ (nM) |
|---|---|---|---|---|---|---|---|
| 1 | F | | | | F | N(CH₃)₂ | 59 ± 7.5 |
| 2a | F | | | | F | NH₂ | 55 ± 7.8 |
| 2b | F | | | | F | NHCH₃ | 23 ± 10.3 |
| 2c | | | | | | N(CH₃)₂ | >3000 |
| 2d | F | | | | | N(CH₃)₂ | 39 ± 6.0 |
| 2e | Cl | | | | | N(CH₃)₂ | 31 ± 3.1 |
| 2f | | F | | | | N(CH₃)₂ | >3000 |
| 2g | | | F | | | N(CH₃)₂ | >3000 |
| 2h | F | F | | | | N(CH₃)₂ | 119 ± 4.6 |
| 2i | F | | F | | | N(CH₃)₂ | 56 ± 8.1 |
| 2j | | F | F | | | N(CH₃)₂ | >3000 |
| 2k | | F | | F | | N(CH₃)₂ | >3000 |
| 2l | F | | | | F | N(CH₃)₂ | 55 ± 6.0 |
| 2m | F | | | | F | N(CH₃)₂ | 23 ± 6.0 |
| 2n | F | | | | Cl | N(CH₃)₂ | 19 ± 5.0 |
| 2o | Cl | | | | Cl | N(CH₃)₂ | 52 ± 7.1 |

SAR studies were undertaken for those diarylacetylenes 2 that possessed fluorine or chlorine substituents in one aryl ring and N-methylamino or N,N-dimethylamino in the other aryl ring. We reported previously that stilbenes repressed colon cancer cell proliferation by inhibiting c-myc expression and inducing the cell cycle inhibitor, p21(Wif1/Cip1). See Zhang et al. *J Med Chem* 2011: 54:1288-1297. The similarity of the diarylacetylenes to the stilbenes also prompted an in silico modeling study of the binding of (E)-4-(2',6'-difluorostyryl)-N,N-dimethylaniline (1) and 4((2,6-difluorophenyl)ethynyl)-N,N-dimethylaniline (2m). It was believed that para-oriented amino-substituents, such as the N-methylamino and N,N-dimethylamino groups, were associated with potent MAT2A inhibition. Using an artificially constructed homodimer of MAT2A, we observed that 1 and 2m bound to the same active site and that diarylacetylene 2m inhibited MAT2 at concentrations comparable to that of the stilbene 1 (data not shown). Variability in the MAT2A inhibition assay made the measurement of c-myc inhibition a preferred analytical tool for assessing the potency of diarylacetylenes.

Figure 2:
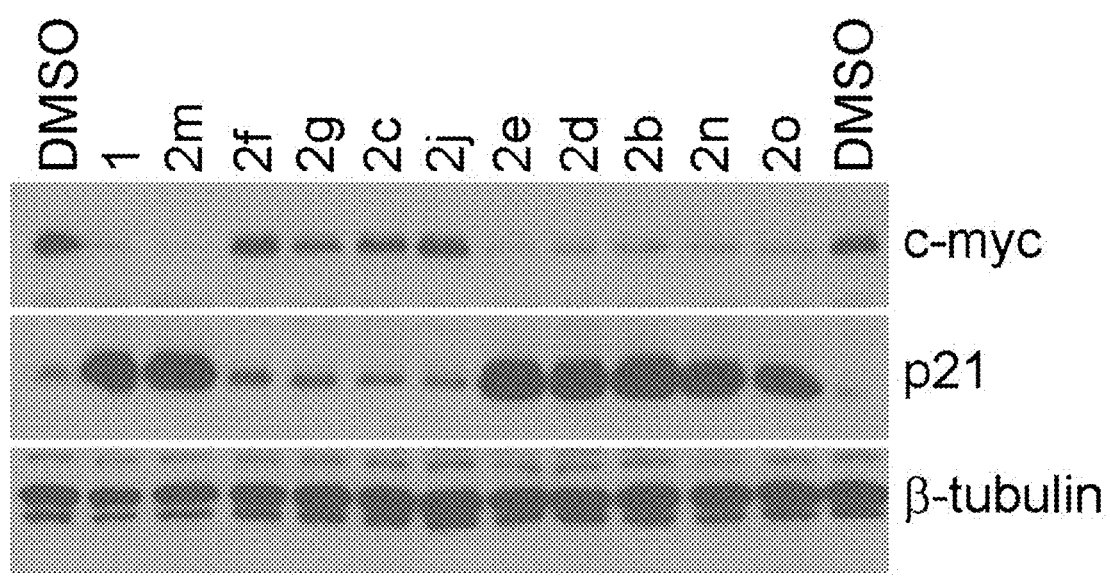
FIG. 2 is a blot showing inhibition of c-myc and induction of p21(Wif1/Cip1) by diarylacetylenes 2 in colon cancer cells. LS174T cells were treated with 1 μM of each diarylacetylenes 2 for 36 h. DMSO and 1 were used as control. Cell lysates were analyzed by western blotting with β-tubulin as a loading control.

We tested the effect of these diarylacetylenes 2 on the proliferation of LS174T colon cancer cells. The expression of c-myc and p21(Wif1/Cip1) were analyzed by western blotting (FIG. 2). The most active diarylacetylenes 2 inhibited c-myc expression at 1 μM concentrations and as expected for a c-myc inhibitor, induced p21(wif1/Cip1) at the same time. Consistent with prior results in the stilbene family, the diarylacetylenes 2 lacking halogen substituents (e.g., 2c) or possessing only one fluorine substituent at a meta- or para-position relative to the acetylenic linkage (e.g., 2g) had very low potency (Table 1). Diarylacetylenes with one or two halogen substituents at ortho-positions relative to the acetylenic linkage (e.g., 2b, 2d, 2e, 2m and 2n) possessed potencies as inhibitors of LS174T cell proliferation that exceeded that of the related stilbene 1 with $IC_{50}$ values less than 50 nM (Table 1). Isomers of these diarylacetylenes (e.g., 2f, 2g, 2j and 2k) with halogens in meta- or para-positions were significantly less active than the diarylacetylenes with ortho-halogens. Once again, these results are in consistent with the SAR findings in the stilbene family of c-myc inhibitors. Zhang et al. *J Med Chem* 2011: 54:1288-1297. Finally, the N-methylation pattern in the diarylacetylenes suggested that N-methyl and N,N-dimethylaniline subunits led to equipotent inhibitors of c-myc (i.e., $IC_{50}$ of 2b≈$IC_{50}$ of 2m) but the desmethyl analog was considerably less active ($IC_{50}$ of 2a=55±7.8 nm).

It was found that diarylacetylenes 2 have a dramatic effect on the proliferation of LS174T colon cancer cells by altering the expression of c-myc and thereby inducing p21(Wif1/Cip1). These results are consistent with similar findings using halogenated stilbenes and suggest that diarylacetylenes and stilbenes repress colon cancer proliferation through similar mechanisms.

In an aspect of the present disclosure, the following particular halogenated diarylacetylenes and their pharmaceutical salts and pharmaceutical compositions can be used to treat cancer, CRC: 4-((2,6-Difluorophenyl)ethynyl)aniline (2a); 4-((2,6-Difluorophenyl)ethynyl)-N-methylaniline (2b); N,N-Dimethyl-4-(phenylethynyl)aniline (2c); 4-((2-Fluorophenyl)ethynyl)-N,N-dimethylaniline (2d); 4-((2-Chlorophenyl)ethynyl)-N,N-dimethylaniline (2e); 4-((3-Fluorophenyl)ethynyl)-N,N-dimethylaniline (2f); 4-((4-Fluorophenyl)ethynyl)-N,N-dimethylaniline (2g); 4-((2,3-Difluorophenyl)ethynyl)-N,N-dimethylaniline (2 h); 4-((2,4-Difluorophenyl)ethynyl)-N,N-dimethylaniline (2i); 4-((3,4-Difluorophenyl)ethynyl)-N,N-dimethylaniline (2j); 4-((3,5-Difluorophenyl)ethynyl)-N,N-dimethylaniline (2k); 4-((2,5-Difluorophenyl)ethynyl)-N,N-dimethylaniline (2l); 4-((2,6-Difluorophenyl)ethynyl)-N,N-dimethylaniline (2m), 4-((2-Chloro-6-fluorophenyl)ethynyl)-N,N-dimethylaniline (2n), and/or 4-((2,6-Dichlorophenyl)ethynyl)-N,N-dimethylaniline (2o).

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Cell Proliferation Assay.

LS174T cells were grown in RPMI medium (Mediatech) supplemented with 5% fetal bovine serum and 1% penicillin/streptomycin. For cell proliferation assays, 3×10$^4$ cells/well growing in 12-well plates were treated with DMSO or inhibitors. The cell numbers and viability were analyzed by Vi-Cell Cell Viability Analyzer after 4 days. The IC$_{50}$ values were calculated with GraphPad Prim 5.

Western Blotting.

Western blot was performed as described previously[1]. The following antibodies were used: anti-c-myc (Epitomics, 1472-1), anti-p21(Wif1/Cip1) (Cell Signaling, 2947), anti-β-tubulin (DSHB, E7).

Materials.

Chemicals were purchased from Sigma Aldrich or Fisher Scientific or were synthesized according to literature procedures. Solvents were used from commercial vendors without further purification unless otherwise noted. Nuclear magnetic resonance spectra were determined on a Varian instrument ($^1$H, 400 MHz; $^{13}$C, 100 Mz). High resolution electrospray ionization (ESI) mass spectra were recorded on a LTQ-Orbitrap Velos mass spectrometer (Thermo Fisher Scientific, Waltham, Mass., USA). The FT resolution was set at 100,000 (at 400 m/z). Samples were introduced through direct infusion using a syringe pump with a flow rate of 5 µL/min. Purity of compounds was established by combustion analyses by Atlantic Microlabs, Inc., Norcross, Ga. Compounds were chromatographed on preparative layer Merck silica gel F254 unless otherwise indicated.

Synthesis of Diarylacetylenes.

A general procedure for the synthesis of diarylacetylenes 2 involved the addition of 2.0 mmol of arylacetylene to a mixture of 2.1 mmol of an aryliodide, 3.0 mmol of diisopropylethylamine, 0.02 mmol of Pd(PPh$_3$)$_4$, and 0.02 mmol of CuI in water (7 mL). The mixture was stirred for 1-2 h at 75° C. After cooling, the product was collected by filtration or extracted using dichloromethane and purified by recrystallization and/or chromatography.

Characterization and Analytical Data Fordiarylacetylenes 2.

4-((2,6-Difluorophenyl)ethynyl)aniline (2a)

Purified by chromatography on silica gel using 1:2ethyl acetate-hexane (R$_f$=0.43). Yield 65%, mp 104-105° C. $^1$H NMR (DMSO-d$_6$): δ 7.46-7.39 (m, 1H), 7.22 (d, 2H, J=8.8 Hz), 7.20-7.16 (m, 2H), 6.58 (d, 2H, J=8.8 Hz), 5.69 (s, 2H, NH$_2$). $^{13}$C NMR (DMSO-d$_6$): δ 161.72 (dd, J$_1$=248.9 Hz, J$_2$=5.3 Hz, two C), 150.21, 132.77 (two C), 129.89 (t, J=9.9 Hz), 113.60 (two C), 111.68 (dd, J$_1$=18.2 Hz, J$_2$=6.1 Hz, two C), 106.96, 101.96 (t, J=19.8 Hz), 102.28 (d, J=2.7 Hz), 73.11. HRMS (ESI) calcd for C$_{14}$H$_9$F$_2$N [MH+]: 230.07758. Found: 230.07660. Anal. Calcd for C$_{14}$H$_9$F$_2$N: C, 73.36; H, 3.96. Found: C, 73.10; H, 4.03.

4-((2,6-Difluorophenyl)ethynyl)-N-methylaniline (2b)

To a solution of 200 mg (0.87 mmol) of 2a in acetone (4 mL) was added successively 145 mg (1.04 mmol, 1.2 equiv) of potassium carbonate and 161 mg (1.13 mmol, 1.3 equiv) of iodomethane. The mixture was refluxed for 5 h. After cooling, the product was diluted with water, extracted with dichloromethane, dried over MgSO$_4$ and concentrated. The product was purified by chromatography on silica gel using 1:5ethyl acetate-hexane (R$_f$=0.48) to afford 68 mg (32%) of 2b. Mp 69-70° C. $^1$H NMR (CDCl$_3$): δ 7.40 (d, 2H, J=8.8 Hz), 7.24-7.15 (m, 1H), 6.92-6.87 (m, 2H), 6.53 (d, 2H, J=8.8 Hz), 3.95 (br s, 1H), 2.84 (s, 3H). $^{13}$C NMR (CDCl$_3$): δ 162.92 (dd, J$_1$=251.2 Hz, J$_2$=5.3 Hz, two C), 149.92, 133.35 (two C), 128.77 (t, J=9.8 Hz), 112.08 (two C), 111.25 (dd, J$_1$=19.0 Hz, J$_2$=6.0 Hz, two C), 110.34, 103.39 (t, J=19.7 Hz), 100.89 (t, J=3.1 Hz), 74.16, 30.48. HRMS (ESI) calcd for C$_{15}$H$_{11}$F$_2$N [MH+]: 244.09323. Found: 244.09241. Anal. Calcd for C$_{15}$H$_{11}$F$_2$N: C, 74.06; H, 4.56. Found: C, 73.89; H, 4.71.

N,N-Dimethyl-4-(phenylethynyl)aniline (2c)

Purified by recrystallization from hexane. Yield 88%, mp 104-106° C. $^1$H NMR (DMSO-d$_6$): δ 7.49-7.47 (m, 2H), 7.41-7.33 (m, 5H), 6.71 (d, 2H, J=9.2 Hz), 2.94 (s, 6H). $^{13}$C NMR (DMSO-d$_6$): δ 150.10, 132.38 (two C), 130.86 (two C), 128.61 (two C), 127.83, 123.29, 111.84 (two C), 108.41, 90.90, 87.16, 39.66 (two C). HRMS (ESI) calcd for C$_{16}$H$_{15}$N [MH+]: 222.12773. Found: 222.12713.

4-((2-Fluorophenyl)ethynyl)-N,N-dimethylaniline (2d)

Purified by recrystallization from hexane. Yield 62%, mp 94-96° C. $^1$H NMR (DMSO-d$_6$): δ 7.57-7.53 (m, 1H), 7.43-7.34 (m, 3H), 7.31-7.22 (m, 1H), 7.24-7.20 (m, 1H), 6.71 (d, 2H, J=9.2 Hz), 2.95 (s, 6H). $^{13}$C NMR (DMSO-d$_6$): δ 161.47 (d, J=246.7 Hz), 150.32, 132.96, 132.46 (two C), 129.91 (d, J=7.6 Hz), 124.64 (d, J=3.8 Hz), 115.55 (d, J=20.5 Hz), 111.81 (two C), 111.63 (d, J=15.2 Hz), 107.83, 96.02 (d, J=3.0 Hz), 80.38, 39.62 (two C). HRMS (ESI) calcd for C$_{16}$H$_{14}$FN [MH+]: 240.11830. Found: 240.11726. Anal. Calcd for C$_{16}$H$_{14}$FN: C, 80.31; H, 5.90. Found: C, 80.04; H, 6.03.

4-((2-Chlorophenyl)ethynyl)-N,N-dimethylaniline (2e)

Purified by recrystallization from ethanol. Yield 56%, mp 108-110° C. $^1$H NMR (DMSO-d$_6$): δ 7.60-7.54 (m, 2H), 7.38-7.34 (m, 4H), 6.73 (d, 2H, J=8.8 Hz), 2.96 (s, 6H). $^{13}$C NMR (DMSO-d$_6$): δ 150.40, 134.00, 133.33, 132.76, 132.55 (two C), 129.28, 127.27, 122.96, 111.85 (two C), 107.80, 96.27, 84.08, 39.67 (two C). HRMS (ESI) calcd for C$_{16}$H$_{14}$ClN [MH+]: 256.08875. Found: 256.08805.

4-((3-Fluorophenyl)ethynyl)-N,N-dimethylaniline (2f)

Purified by recrystallization from hexane. Yield 87%, mp 99-100° C. $^1$H NMR (DMSO-d$_6$): δ 7.45-7.31 (m, 5H), 7.22-7.17 (m, 1H), 6.71 (d, 2H, J=9.2 Hz), 2.95 (s, 6H). $^{13}$C NMR (DMSO-d$_6$): δ 161.90 (d, J=242.8 Hz), 150.30, 132.55 (two C), 130.66 (d, J=8.4 Hz), 127.19 (d, J=2.2 Hz), 125.32 (d, J=9.9 Hz), 117.31 (d, J=22.7 Hz), 115.02 (d, J=21.3 Hz), 111.81 (two C), 107.79, 92.09, 86.07 (d, J=3.0 Hz), 39.64 (two C). HRMS (ESI) calcd for $C_{16}H_{14}FN$ [MH+]: 240.11830. Found: 240.11750. Anal. Calcd for $C_{16}H_{14}FN$: C, 80.31; H, 5.90. Found: C, 80.03; H, 6.10.

4-((4-Fluorophenyl)ethynyl)-N,N-dimethylaniline (2g)

Purified by recrystallization from methanol. Yield 92%, mp 132-134° C. $^1H$ NMR (DMSO-$d_6$): δ 7.54-7.51 (m, 2H), 7.35 (d, 2H, J=8.8 Hz), 7.24-7.20 (m, 2H), 6.70 (d, 2H, J=9.2 Hz), 2.94 (s, 6H). $^{13}C$ NMR (DMSO-$d_6$): δ 161.47 (d, J=245.1 Hz), 150.12, 133.07 (d, J=8.4 Hz, two C), 132.35 (two C), 119.74 (d, J=3.8 Hz), 115.80 (d, J=22.1 Hz, two C), 111.83 (two C), 108.26, 90.56, 86.07, 39.65 (two C). HRMS (ESI) calcd for $C_{16}H_{14}FN$ [MH+]: 240.11830. Found: 240.11752.

4-((2,3-Difluorophenyl)ethynyl)-N,N-dimethylaniline (2 h)

Purified by recrystallization from methanol. Yield 65%, mp 104-106° C. $^1H$ NMR (DMSO-$d_6$): δ 7.46-7.37 (m, 4H), 7.24-7.19 (m, 1H), 6.72 (d, 2H, J=8.0 Hz), 2.91 (s, 6H). $^{13}C$ NMR (DMSO-$d_6$): δ 149.78 (dd, $J_1$=244.4 Hz, $J_2$=11.4 Hz), 149.37 (dd, $J_1$=247.1 Hz, $J_2$=13.8 Hz), 132.62 (two C), 128.15 (d, J=4.0 Hz), 125.14 (d, J=4.6 Hz), 125.06 (d, J=4.6 Hz), 117.21 (d, J=16.7 Hz), 113.87 (d, J=11.4 Hz), 111.80 (two C), 107.20, 97.54 (d, J=3.8 Hz), 79.23 (d, J=4.6 Hz), 39.60 (two C). HRMS (ESI) calcd for $C_{16}H_{13}F_2N$ [MH+]: 258.10888. Found: 258.10818. Anal. Calcd for $C_{16}H_{13}F_2N$: C, 74.69; H, 5.09. Found: C, 74.43; H, 5.22.

4-((2,4-Difluorophenyl)ethynyl)-N,N-dimethylaniline (2i)

Purified by recrystallization from methanol. Yield 82%, mp 116-118° C. $^1H$ NMR (DMSO-$d_6$): δ 7.65-7.59 (m, 1H), 7.40-7.34 (m, 3H), 7.15-7.11 (m, 1H), 6.71 (d, 2H, J=9.2 Hz), 2.95 (s, 6H). $^{13}C$ NMR (DMSO-$d_6$): δ 161.79 (dd, $J_1$=249.3 Hz, $J_2$=12.5 Hz), 150.35, 161.63 (dd, $J_1$=247.8 Hz, $J_2$=11.8 Hz), 134.11 (dd, $J_1$=9.8 Hz, $J_2$=2.3 Hz), 132.44 (two C), 112.15 (dd, $J_1$=22.0 Hz, $J_2$=3.8 Hz), 111.81 (two C), 108.31 (dd, $J_1$=15.6 Hz, $J_2$=4.2 Hz), 107.68, 104.50 (t, J=25.8 Hz), 95.75, 79.35, 39.63 (two C). HRMS (ESI) calcd for $C_{16}H_{13}F_2N$ [MH+]: 258.10888. Found: 258.10806. Anal. Calcd for $C_{16}H_{13}F_2N$: C, 74.69; H, 5.09. Found: C, 74.61; H, 5.23.

4-((3,4-Difluorophenyl)ethynyl)-N,N-dimethylaniline (2j)

Purified by recrystallization from methanol. Yield 93%, mp 100-101° C. $^1H$ NMR (DMSO-$d_6$): δ 7.60-7.55 (m, 1H), 7.48-7.41 (m, 1H), 7.37-7.32 (m, 3H), 6.71 (d, 2H, J=9.2 Hz), 2.95 (s, 6H). $^{13}C$ NMR (DMSO-$d_6$): δ 150.29, 149.21 (dd, $J_1$=249.0 Hz, $J_2$=14.5 Hz, two C), 132.49 (two C), 128.26 (dd, $J_1$=6.4 Hz, $J_2$=3.4 Hz), 128.68 (dd, $J_1$=8.0 Hz, $J_2$=4.2 Hz), 119.76 (d, J=18.2 Hz), 118.00 (d, J=16.7 Hz), 111.80 (two C), 107.69, 91.58, 85.21, 39.62 (two C). HRMS (ESI) calcd for $C_{16}H_{13}F_2N$ [MH+]: 258.10888. Found: 258.10787. Anal. Calcd for $C_{16}H_{13}F_2N$: C, 74.69; H, 5.09. Found: C, 74.80; H, 5.11.

4-((3,5-Difluorophenyl)ethynyl)-N,N-dimethylaniline (2k)

Purified by recrystallization from methanol. Yield 84%, mp 72-74° C. $^1H$ NMR (DMSO-$d_6$): δ 7.37 (d, 2H, J=8.8 Hz), 7.28-7.19 (m, 3H), 6.71 (d, 2H, J=9.2 Hz), 2.96 (s, 6H). $^{13}C$ NMR (DMSO-$d_6$): δ 162.27 (dd, $J_1$=245.1 Hz, $J_2$=14.4 Hz, two C), 150.47, 132.70 (two C), 126.29 (t, J=12.1 Hz), 113.95 (dd, $J_1$=19.0 Hz, $J_2$=7.6 Hz, two C), 111.78 (two C), 107.22, 103.94 (t, J=25.8 Hz), 93.42, 85.33 (t, J=3.8 Hz), 39.60 (two C). HRMS (ESI) calcd for $C_{16}H_{13}F_2N$ [MH+]: 258.10888. Found: 258.10787. Anal. Calcd for $C_{16}H_{13}F_2N$: C, 74.69; H, 5.09. Found: C, 74.43; H, 5.20.

4-((2,5-Difluorophenyl)ethynyl)-N,N-dimethylaniline (2l)

Purified by recrystallization from methanol. Yield 79%, mp 106-107° C. $^1H$ NMR (DMSO-$d_6$): δ 7.45-7.41 (m, 1H), 7.39-7.32 (m, 3H), 7.28-7.22 (m, 1H), 6.72 (d, 2H, J=9.2 Hz), 2.96 (s, 6H). $^{13}C$ NMR (DMSO-$d_6$): δ 157.89 (dd, $J_1$=243.6 Hz, $J_2$=2.3 Hz), 157.80 (dd, $J_1$=239.9 Hz, $J_2$=2.3 Hz), 150.52, 132.62 (two C), 118.82 (d, J=25.8 Hz), 117.04 (dd, $J_1$=24.3 Hz, $J_2$=9.1 Hz), 116.53 (dd, $J_1$=24.3 Hz, $J_2$=8.3 Hz), 113.01 (dd, $J_1$=18.2 Hz, $J_2$=10.7 Hz), 111.80 (two C), 107.23, 97.22 (d, J=3.8 Hz), 79.61, 39.61 (two C). HRMS (ESI) calcd for $C_{16}H_{13}F_2N$ [MH+]: 258.10888. Found: 258.10812. Anal. Calcd for $C_{16}H_{13}F_2N$: C, 74.69; H, 5.09. Found: C, 74.56; H, 5.21.

4-((2,6-Difluorophenyl)ethynyl)-N,N-dimethylaniline (2m)

Purified by recrystallization from hexane. Yield 59%, mp 98-100° C. $^1H$ NMR (DMSO-$d_6$): δ 7.49-7.41 (m, 1H), 7.37 (d, 2H, J=8.8 Hz), 7.23-7.18 (m, 2H), 6.72 (d, 2H, J=8.8 Hz), 2.97 (s, 6H). $^{13}C$ NMR (DMSO-$d_6$): δ 161.75 (dd, $J_1$=248.9 Hz, $J_2$=5.3 Hz, two C), 150.58, 132.59 (two C), 130.12 (t, J=10.3 Hz), 111.76 (dd, $J_1$=17.9 Hz, $J_2$=4.3 Hz, two C), 111.82 (two C), 107.21, 101.83 (t, J=19.8 Hz), 100.88 (t, J=3.1 Hz), 73.83, 39.64 (two C). HRMS (ESI) calcd for $C_{16}H_{13}F_2N$ [MH+]: 258.10888. Found: 258.10801. Anal. Calcd for $C_{16}H_{13}F_2N$: C, 74.69; H, 5.09. Found: C, 74.47; H, 5.24.

4-((2-Chloro-6-fluorophenyl)ethynyl)-N,N-dimethylaniline (2n)

Purified by chromatography on silica gel using 1:5 ethyl acetate-hexane ($R_f$=0.74). Yield 53%, mp 86-88° C. $^1H$ NMR (DMSO-$d_6$): δ 7.45-7.30 (m, 5H), 6.73 (d, 2H, J=8.8 Hz), 2.97 (s, 6H). $^{13}C$ NMR (DMSO-$d_6$): δ 161.89 (d, J=249.7 Hz), 150.62, 135.11 (d, J=3.0 Hz), 132.64 (two C), 129.90 (d, J=9.1 Hz), 125.37 (d, J=3.0 Hz), 114.37 (d, J=21.2 Hz), 112.37 (d, J=18.2 Hz), 111.84 (two C), 107.24, 101.55 (d, J=3.8 Hz), 77.59, 39.64 (two C). HRMS (ESI) calcd for $C_{16}H_{13}ClFN$ [MH+]: 274.07933. Found: 274.07858. Anal. Calcd for $C_{16}H_{13}ClFN$: C, 70.20; H, 4.79. Found: C, 70.43; H, 4.76.

4-((2,6-Dichlorophenyl)ethynyl)-N,N-dimethylaniline (2o)

Purified by recrystallization from ethanol. Yield 54%, mp 96-98° C. $^1H$ NMR (DMSO-$d_6$): δ 7.52 (d, 2H, J=8.0 Hz), 7.37-7.29 (m, 3H), 6.70 (d, 2H, J=9.2 Hz), 2.93 (s, 6H). $^{13}C$ NMR (DMSO-$d_6$): δ 150.66, 135.26, 133.31, 132.67 (two C), 129.40, 127.97 (two C), 122.79, 111.82 (two C), 107.22, 101.91, 81.62, 39.61 (two C). HRMS (ESI) calcd for $C_{16}H_{13}Cl_2N$ [MH+]: 290.04978. Found: 290.04888. Anal. Calcd for $C_{16}H_{13}Cl_2N$: C, 66.22; H, 4.52. Found: C, 66.06; H, 4.70.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A method of treating colorectal cancer, the method comprising administering to a patient in need of such treatment an effective amount of a compound according to the following formula:

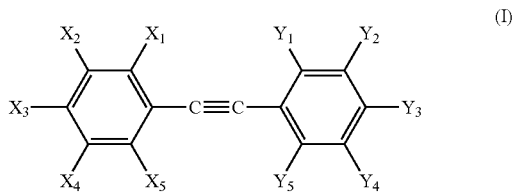

(I)

or a pharmaceutically acceptable salt thereof, wherein each of $X_1$ through $X_5$ independently represents H, a lower alkyl, or halo, provided that at least one of $X_1$ through $X_5$ is a halo; and each of $Y_1$ through $Y_5$ independently represents H, a lower alkyl, or $NR_1R_2$, provided that at least one of $Y_1$ through $Y_5$ is $NR_1R_2$, wherein each of $R_1$ and $R_2$ independently represents H, or a lower alkyl, provided that at least one of $R_1$ or $R_2$ is a lower alkyl.

2. The method of claim 1, wherein at least two of $X_1$ through $X_5$ are halo groups.

3. The method of claim 2, wherein $X_1$ through $X_5$ are either (i) a fluoro and chloro, (ii) both fluoro, or (iii) both chloro groups.

4. The method of claim 1, wherein both $R_1$ and $R_2$ are lower alkyl groups.

5. The method of claim 4, wherein either $X_1$ or $X_5$ or both $X_1$ and $X_5$ are halo groups and $X_2$ through $X_4$ are H or a lower alkyl.

6. The method of claim 1, wherein $X_1$ and/or $X_5$ are halo groups, $X_2$ through $X_4$ are H or a lower alkyl, $Y_3$ is $NR_1R_2$, and $Y_1$, $Y_2$, $Y_4$, and $Y_5$ independently represent H or a lower alkyl.

7. The method of claim 1, wherein $X_1$ and/or $X_5$ are fluoro and/or chloro and at least one of $R_1$ or $R_2$ is a lower alkyl.

8. A pharmaceutical composition comprising a therapeutically effective amount of a compound according to the following formula:

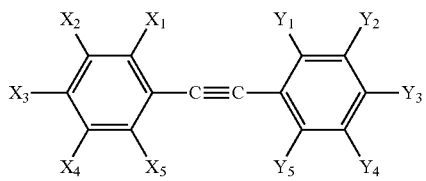

or a pharmaceutically acceptable salt thereof, wherein each of $X_1$ through $X_5$ independently represents H, a lower alkyl, a fluoro or a chloro, provided that at least one of $X_1$ through $X_5$ is a fluoro or chloro; and each of $Y_1$ through $Y_5$ independently represents H, a lower alkyl, or $NR_1R_2$, provided that at least one of $Y_1$ through $Y_5$ is $NR_1R_2$, wherein each of $R_1$ and $R_2$ independently represents H, or a lower alkyl, provided that at least one of $R_1$ or $R_2$ is a lower alkyl; and a pharmaceutically acceptable carrier, wherein the pharmaceutical composition is acceptable to be administered to a mammal.

9. The pharmaceutical composition of claim 8, wherein at least two of $X_1$ through $X_5$ are fluoro, or chloro groups and the remaining $X_1$ through $X_5$ are H.

10. The pharmaceutical composition of claim 8, wherein $X_1$ and $X_5$ are either (i) a fluoro and chloro, (ii) both fluoro, (iii) both chloro groups.

11. The pharmaceutical composition of claim 8, wherein at least one of $R_1$, or $R_2$, is a lower alkyl.

12. The pharmaceutical composition of claim 11, wherein the lower alkyl is methyl or ethyl.

* * * * *